US006897035B1

(12) United States Patent
Csöregi et al.

(10) Patent No.: US 6,897,035 B1
(45) Date of Patent: May 24, 2005

(54) BIOSENSOR

(75) Inventors: Elisabeth Csöregi, Lund (SE); Mihaela Niculescu, Lund (SE); Ivo Frebort, Olomouc (CZ)

(73) Assignee: Forskarpatent I SYD AB, Lund (SE)

( * ) Notice: Subject to any disclaimer, the term of this patent is extended or adjusted under 35 U.S.C. 154(b) by 0 days.

(21) Appl. No.: 10/019,651

(22) PCT Filed: Jul. 6, 2000

(86) PCT No.: PCT/SE00/01449

§ 371 (c)(1),
(2), (4) Date: Jul. 8, 2002

(87) PCT Pub. No.: WO01/02827

PCT Pub. Date: Jan. 11, 2001

(30) Foreign Application Priority Data

Jul. 6, 1999 (SE) .............................................. 9902608

(51) Int. Cl.$^7$ ............................ C12Q 1/26; C12Q 1/28; C12N 1/00; G01N 33/68
(52) U.S. Cl. ............................. 435/25; 435/7.9; 435/28; 435/817
(58) Field of Search ......................... 435/25, 28, 283.1, 435/287.1, 287.9, 817, 7.9

(56) References Cited

U.S. PATENT DOCUMENTS

| 5,378,628 A | | 1/1995 | Gräatzel et al. | |
| 5,565,329 A | * | 10/1996 | Ohashi et al. | ................. 435/25 |
| 5,846,702 A | | 12/1998 | Deng et al. | |

FOREIGN PATENT DOCUMENTS

| WO | WO 93/23748 | * | 11/1993 | ......... G01N/27/327 |

OTHER PUBLICATIONS

Cogoni et al., "Amine Oxidase from *Lathyrus cicera* and *Phaseolus vulgaris*: Purification and Properties" (1989) Prep. Biochem., 19:95–112, description accessed on the Internet Jul. 21, 2003 at www.brenda.uni–koeln.de/php/lit.php4?e=1.4.3.6&r=34.*

McIntire, W.S., "Newly Discovered Redox Cofactors: Possible Nutritional, Medical, and Pharmacological Relevance to Higher Animals" (Jul. 1998) Annual Review of Nutrition, vol. 18, pp. 145–177, Abstract.*

Anon., "NiceZyme View of ENZYME: EC 1.4.3.6" accessed on the Internet on Jul. 21, 2003 at www.expasy.org/cgi–bin/nicezyme.pl?1.4.3.6.*

Nicolescu et al., Anal. Chem. 2000, 72, entitled, "Redox Hydrogel–Based Amperometric Bienzyme Electrodes for Fish Freshness Monitoring," pp. 1591–1597.

Nicolescu et al., Electroanalysis 2000, vol. 12, No. 5, entitled "Amine Oxidase Based Amperometric Biosensors for Histamine Detection," pp. 369–375.

Tombelli et al., Analytica Chimica Acta, vol. 358, (1998), entitled, "Electrochemical Biosensors for Biogenic Amines: A comparison between different approaches," pp. 277–284.

Bonovette et al., Enzyme and Microbial Technology 20:32–38, 1997, entitled, "Amperometric Biosensor for Diamine Using Diamine Oxidase Purified from Porcine Kidney," pp. 33–38.

Chennitius et al., Sensors and Actuators B 32 (1196), entitled, "Development of Screen–Printed Enzyme Electrodes for the Estimation of fish Quality," pp. 107–113.

Male et al., Journal of Food Science, vol. 61, No. 5, 1996, entitled, "Amperometric Biosensor for Total Histamine, Putrescine and Cadaverine Using Diamine Oxidase," pp. 1012–1016.

Proisi, et al., Food Chemistry, vol. 62, No. 2, 1998, entitled, "Determination of Biogenic Amines with an Electrochemical Biosensor and its Application to Salted Anchovies," pp. 225–232.

* cited by examiner

Primary Examiner—Jean C. Witz
Assistant Examiner—Susan Hanley
(74) Attorney, Agent, or Firm—McDermott Will & Emery LLP

(57) ABSTRACT

The present invention relates to a biosensor for the detection and/or the determination of freshness biomarkers, such as biogenic amines (preferably histamine) in food and beverage, comprising an electrode and a mono-enzyme system, such as an amine oxidase, or a bi-enzyme system of an amine oxidase and a peroxidase. The enzymes are optionally crosslinked into an osmium based redox polymer.

6 Claims, 3 Drawing Sheets

BIOSENSOR

The present invention relates to a biosensor, which includes an electrode and a mono-enzyme- or a bi-enzyme-system and uses of the biosensor.

BACKGROUND OF THE INVENTION

Rapid evaluation of food and beverage, such as fish, meat, quality is required in food industry. The biogenic amine content in food has been intensively studied because of their potential toxicity. Histamine is the most biologically active compound from this class, affecting the normal functions of the heart; smooth muscle, motor neurones, and gastric acid secretion. Other biogenic amines, such as putrescine and cadaverine, may amplify the effects caused by histamine intoxication, inhibiting the enzymes involved in histamine biodegradation: diamine oxidase and histamine-N-methyl transferase.

Numerous countries adopted maximum levels for histamine in food, especially in fish products. The Italian law has fixed a level of 100 mg/kg food, and similar limits have been adopted by EEC regulations.

Therefore, there is a need for developing of simple and inexpensive methods for determining of freshness biomarkers. Freshness biomarkers comprising inositol monophosphate, hypoxanthine and xanthine, these are intermediate degradation products of nucleic acids or biogenic amines, which are produced by microbial decarboxylation of the amino acids, histidine, ornithine, and lysine.

Classical methods for the determination of the content of biogenic amines are chromatographic techniques, such as gas chromatography, thin layer chromatography, reversed phase liquid chromatography, and liquid chromatography. However, these often require sample pre-treatment and relatively long analysing time, which leads to high costs and make these methods not suitable for routine use.

From U.S. Pat. No. 5,565,329 is a method for determination of histamine concentration in a sample by determination of the decrease in dissolved oxygen (DO) known. The method involves adding a solution of an enzymatic reagent, which have a histamine oxidase activity, into an examination liquid containing the test sample and detect the sensor output signal. The analyser has a reaction cell provided with a DO electrode. The enzymatic reagent is a Cu-containing fungal amine oxidase. Which is extracted from a cellmass belonging to *Aspergillus Niger* cultured in a culture medium including amine as a nitrogen source. This approach is not very selective and sensitive.

Enzymatic determination of biogenic amines represents an alternative that can solve the above mentioned problems. However, most of the amino oxidase biosensors require a high operating potential (>500 mV vs. Ag/AgCl), which can lead to high background currents and low selectivity due to bias signals caused by electrochemically easily oxidisable interferences, which are always present in complex matrices, such as food or beverage.

SUMMARY OF THE INVENTION

As is clear from the description above a rapid, accurate, simple and handy analytical instrumental tool is needed for determination of food hygiene all along the food process line, starting from the source to the consumer.

With the present invention the above mentioned problems have been solved, the present invention offers a highly sensitive, selective rapid and very convenient determination and/or detection of the biomarkers in very small amounts.

Thus, the present invention relates to a biosensor for detection and/or determination of the content of freshness biomarkers in food or beverage. The biosensor comprises an electrode and a copper-containing amine oxidase derived from grass pea (AO, E. C. 1.4.3.6) in a mono-enzyme system, or in a bi-enzyme system containing said amine oxidase coupled with a peroxidase.

The mono-enzyme system comprising said copper containing amine oxidase (AO) represents one preffered embodiment of the invention. The amine oxidase may be isolated from grass pea and purified according to Sebela, M., et al, Phytochem. Anal. 1998, 9, 211–222.

Another preferred embodiment of the present invention is the biosensor comprising the bi-enzyme system comprising said copper containing amine oxidase (AO) coupled with a peroxidase (PO) such as horseradish (HRP), soybean, tobacco, sweet potato or palmtree peroxidase.

Another preferred embodiment of the present invention the mono-enzyme- or the bi-enzyme-system is crosslinked into an osmium redox polymer. The osmium-based redox polymer is preferably ($PVI_{13}$-dmeOs) of poly-(1-vinyl-imidazole), complexed with [Os-(4,4'-dimethyl-bipyridine)$_2$Cl]$^{+/+2}$, and a crosslinking agent such as poly-(ethyleneglycol)-diglycidyl-ether (PEGDGE).

Yet another embodiment of the present invention is the use of the biosensor as an analytical tool in the determination and/or detection of the freshness biomarkers in food.

Other uses and preferred embodiments of the present invention are defined in the use-claims and the subclaims.

DETAILED DESCRIPTION OF THE INVENTION

Amine oxidase represents a class of enzymes with a ubiquitous distribution in mammals, plants and microorganisms. However, the structure, selectivity and biological functions are very different, depending on the isolation source. Grass-pea amine oxidase, for instance, is a copper-containing amino oxidase, which besides the metal ions also contains an organic cofactor with a quinoide structure (topa-quinone) in its catalytic site.

In methods, where an amine oxidase is used, the enzyme is converting the amine to the corresponding aldehyde, with $NH_3$ and $H_2O_2$ release, according to the following reaction I:

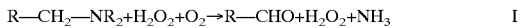

$$R\text{—}CH_2\text{—}NR_2+H_2O_2+O_2 \rightarrow R\text{—}CHO+H_2O_2+NH_3 \qquad I$$

Both oxygen consumption and hydrogen peroxide formation have been used for monitoring of biogenic amines on the basis of the above mentioned reaction.

It has surprisingly been shown that the interaction between the material of the electrode and the enzyme(s) resulted in a very selective and sensitive biosensor. The electrode has to be of any electron conducting material, such as noble metals, carbon/graphite-based material, conducting salts, conducting polymers etc.

The mono-enzyme based biosensor according to the present invention is based either on the amine oxidase immobilised on top of an electrode (DET, direct electron transfer mechanism) or on amine oxidase crosslinked into a redox hydrogel forming a coating layer on top of an electrode (MET, mediated electron transfer mechanism).

According to the bi-enzymatic approach of the invention, the bi-enzyme electrode configuration is based on the enzyme amine oxidase (AO), from grass pea, and horseradish peroxidase (HRP) on a solid graphite electrode. The bi-enzymatic system is working at a potential where biases are minimal. The bi-enzyme electrodes were prepared either by simply adsorbing the two enzymes on the electrode surface (DET) or by crosslinking them into a redox polymer (MET). In the latter case, the highly permeable and stable redox hydrogel is formed of a poly(1-vinylimidazole) complexed with [Os-(4,4'-dimethylbipyridine)$_2$Cl]$^{+/+2}$ ($PVI_{13}$-dmeOs), and crosslinked to the enzymes by a crosslinking agent, e.g. poly-(ethyleneglycol)-diglycidyl-ether (PEGDGE).

The optimal biosensor design was evaluated in terms of sensitivity, selectivity, life- and response-time, and it was used for the analysis of fish samples stored under different conditions.

In the DET reaction mechanism, the biosensor of the present invention amine oxidase first converts the amine substrate (e.g. histamine) to an aldehyde product, the active form of the enzyme being recovered by oxidation of the organic cofactor in presence of molecular oxygen according to reaction mechanism II:

Redox hydro-gels are an effective matrix for enzyme immobilisation resulting in increased stability and the enhanced rates of the electron transfer. The rate of the electron transfer is highly influenced by the composition of the redox hydrogel, as well as by the kinetics of the used enzyme(s). Therefore various biosensor designs were considered in order to find the optimal electrode structure displaying the most efficient rate of electron transfer.

The structure of the redox polymer [Os-(4,4'-dimethyl-bipyridine)$_2$Cl complexed to poly(1-vinyl-imidazole)] is shown in the following formula:

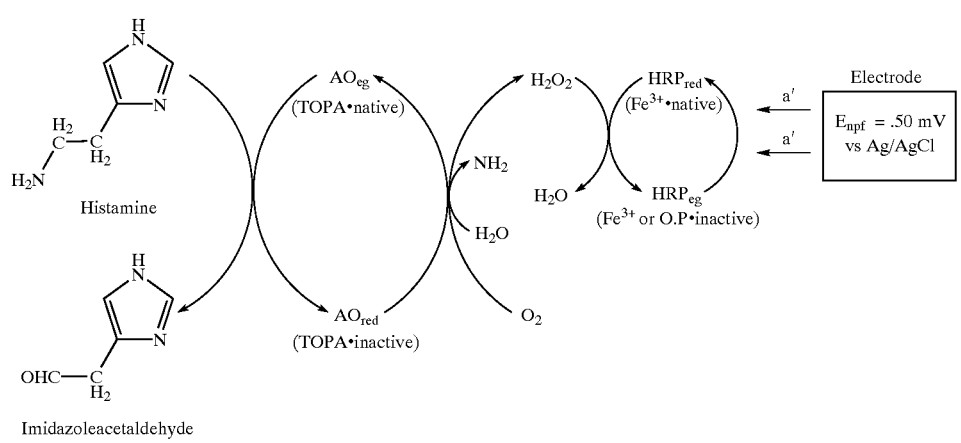

II

The hydrogen peroxide formed during the first reaction is subsequently reduced to water by the action of peroxidase. The native form of the second enzyme is re-made either by direct reduction of its heme cofactor on the electrode surface or by receiving electrons from a mediator, maintained in it's reduced form by the potential applied on the graphite electrode (50 mV vs. Ag/AgCl).

The peroxidase is either reduced by direct reduction of its heme cofactor (reaction mechanism II) or by receiving electrons from a mediator (MET), such as an osmium based redox polymer (see reaction mechanism III), maintained in its reduced form by the potential applied.

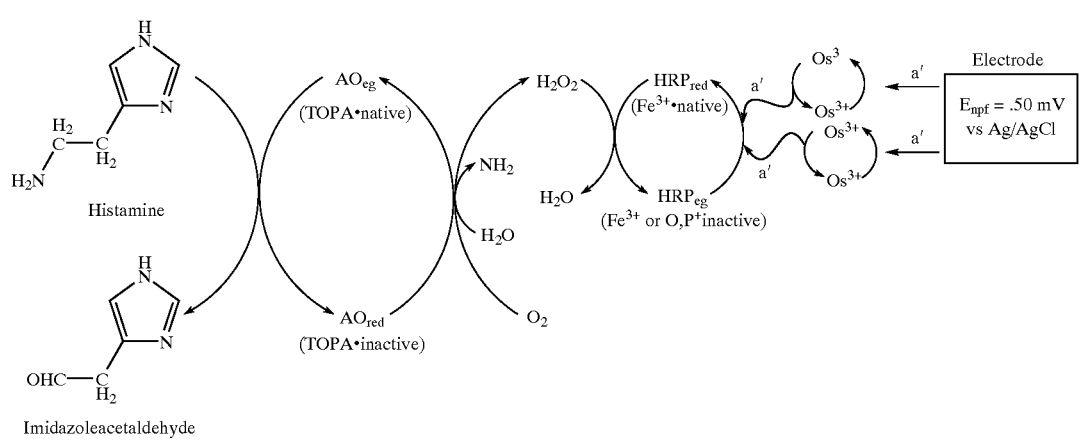

III

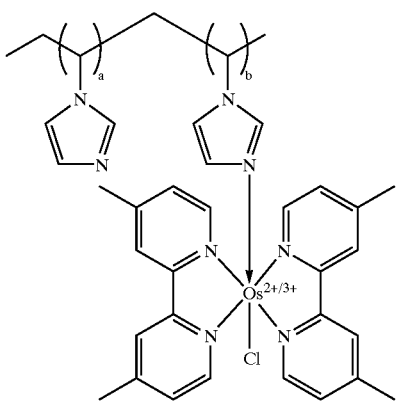

The mono-enzyme- or the bi-enzyme-system is applied on to the electrode in three different ways (type I, II and III). In the following, enzyme means mono-enzyme—or Li-enzyme—system if not otherwise is stated.

Biosensor Type I: the enzyme is applied direct on to the electrode surface (DET). The reaction follows reaction mechanism II.

Biosensor Type II: the enzyme is entrapped in a redox hydrogel and applied on the top of the electrode (MET, one layer electrode). The reaction follows reaction mechanism III.

Biosensor Type III: represent a sequential coating procedure of enzyme and redox polymer (MET, bilayer electrode). The reaction follows also reaction mechanism III.

In order to achieve an effective electron transfer all types of biosensors were optimised with regard to amount of immobilised enzyme and ratio of the used enzyme (Type I), composition of enzymes: redox polymer: crosslinking agent (Type II) and influence of electrode coating procedures (Type III).

Preparation of Biosensors

The biosensors were prepared by modifying graphite electrodes, which were prepared as follows:

i) Rods of spectroscopic graphite (Ringsdorff Werke GmbH, Bonn, Germany, type RW001, 3.05 mm diameter) were cut, and polished on a wet fine emery paper (Tufback, Durite P1200, Allar, Sterling Heights, Mich.).

ii) The electrode surface was rinsed with water, dried at room temperature before coating with the enzymes. Three different electrode types were prepared:

Type I electrodes: were prepared by placing 6 µl of a premixed solution containing various amounts of AO (stock 20 mg/ml in phosphate buffer 0.1 M, pH 7.2 (PB)) and HRP (stock 10-mg/ml in PB) on the graphite electrode.

Type II electrodes were prepared by cross-linking 6 µl of a mixture formed of AO (stock solution 20 mg/ml in PB), HRP (stock 10 mg/ml in PB) with an osmium redox hydrogel. The osmium redox consisted hydrogel consisted of $PVI_{13}$-dmeOS (stock 10 mg/ml in PB) and PEGDGE (5 mg/ml freshly prepared and used within 15 min). The bi-enzyme cross-linked into the redox hydrogel was placed on the top of the graphite electrode in different ratios in % by weight (w/w).

Type III electrodes: was prepared using a sequential coating procedure.

Type III a—first a premixed solution 6 µl of $HRP_{13}$-dmeOs, and PEGDGE was placed on the top of the electrode. Next, the electrodes were dried for 1 hour before coating with 6 µl of AO (see table III).

Type III b—first a solution of 6 µl of AO was placed on the top of the electrode. After drying for 1 hour, the electrodes were coated with 6 µl of a premixed solution of HRP, $PV_{13}$-dmeOs, and PEGDGE.

Type III c—in the first step, a drop of HRP solution (6 µl) was placed on the top of the electrode, and after its drying, a second layer containing 6 µl of a premixed solution of AO, $PVI_{13}$-dmeOs, and PEGDGE was added.

Type III d—first a premixed solution of 6 µl of AO, $PV_{13}$-dmeOs, and PEGDGE was placed on the top of the electrode. Next, electrodes were dried for 1 hour before coating 6 µl of HRP.

If not otherwise stated, all modified electrodes were stored at 4° C. for 14 h in a glass beaker and were rinsed with PB before use.

The bi-enzyme graphite electrodes were inserted as the working electrode in three electrode cell of wall jet-type placed in a single channel flow-injection system containing a manual sample injection valve (Valco Instruments Co. Inc., Houston, Tex., USA) and a 50 µl injection loop.

A peristaltic pump (Alitea AB, Stockholm, Sweden) was used to pump the carrier solution at desired flow rates through Teflon tubings (0.5 mm i.d.) to the flow cell. A potentionstat (Zäta-Elektronik, Höör, Sweden) maintained the constant potential between the working and the reference electrode Ag/AgCl (0.1 M KCl). A platinum wire was used as the counter electrode. The response current was monitored with a single channel recorder (Model BD 111, Kipp & Zonen, Delft, The Netherlands).

Operational stability experiments were made using an Automated Sample Injection Analyser (Ismatec, Glattgurg-Zürich, Switzerland) by injecting samples of 100 µM histamine and 50 µM putrescine respectively, with a sample through-put of 30 injections/h using PB as the carrier solution at a flow rate of 0.5 ml/min.

The increasing tendency of the apparent Michaelis-Menten constant with the amount of immobilised horseradish peroxidase was attributed to an increase in the thickness of the total protein loading on the electrode surface. The reducing the analytes diffusion rate in the film is effected by the influence of the protein loading. The maximum current, as well as the biosensors sensitivity trend show that the best combination is the one containing 80% by weight amine oxidase and 20% by weight horseradish peroxidase, which has been considered for the further experiments. The dynamic range for all the studied biosensors of Type I was 1–100 µM for both histamine and putrescine.

Different characteristics of Type I biosensors were measured and calculated for different ratios of amine oxidase AO and horseradish peroxidase HRP. The values are introduced into table I. Where $I_{max}$ and $K_m^{app}$ values are estimated from Michaelis-Menten equation:

$$I=(I_{max}\times[A])/(K_m^{app}+[A])$$

In table I: A is analyte, S is the sensitivity, calculated as $I_{max}/K_m^{app}$, C is the conversion, calculated as $S_{analyte}/S_{H2O2}$ and DL is the detection limit, calculated as 3 S/N (signal-to-noise ratio).

TABLE I

| Type of electrode (w/w) | Analyte | $K_m^{app}$ ($\mu M$) | $I_{max}$ ($\mu A$) | S (mA/Mcm$^2$) | C (%) | DL ($\mu M$) |
|---|---|---|---|---|---|---|
| AO 87% | Histamine | 279 ± 16 | 1.03 ± 0.02 | 50.57 ± 0.82 | 19.0 | 0.16 |
| HRP 13% | Putrescine | 153 ± 15 | 1.96 ± 0.06 | 175.48 ± 1.40 | 66.2 | 0.06 |
| | $H_2O_2$ | 93 ± 3 | 1.80 ± 0.21 | 265.13 ± 1.65 | — | — |
| AO 80% | Histamine | 332 ± 17 | 1.34 ± 0.03 | 55.28 ± 0.76 | 16.6 | 0.20 |
| HRP 20% | Putrescine | 228 ± 15 | 3.01 ± 0.07 | 180.84 ± 0.95 | 54.7 | 0.07 |
| | $H_2O_2$ | 112 ± 8 | 2.07 ± 0.06 | 330.23 ± 1.02 | — | — |
| AO 67% | Histamine | 370 ± 22 | 1.30 ± 0.03 | 48.13 ± 0.14 | 14.7 | 0.25 |
| HRP 33% | Putrescine | 240 ± 15 | 3.10 ± 0.01 | 176.94 ± 0.87 | 54.2 | 0.07 |
| | $H_2O_2$ | 153 ± 6 | 3.64 ± 0.04 | 325.90 ± 0.56 | — | — |
| AO 50% | Histamine | 437 ± 43 | 1.22 ± 0.04 | 38.24 ± 1.42 | 12.7 | 0.33 |
| HRP 50% | Putrescine | 268 ± 23 | 3.05 ± 0.10 | 155.90 ± 1.26 | 52.0 | 0.08 |
| | $H_2O_2$ | 175 ± 8 | 3.83 ± 0.05 | 299.80 ± 0.65 | — | — |
| AO 40% | Histamine | 441 ± 23 | 1.16 ± 0.02 | 36.03 ± 0.75 | 10.9 | 0.34 |
| HRP 60% | Putrescine | 276 ± 22 | 3.69 ± 0.06 | 183.14 ± 1.11 | 55.7 | 0.13 |
| | $H_2O_2$ | 206 ± 3 | 4.94 ± 0.03 | 328.50 ± 0.22 | — | — |
| AO 33% | Histamine | 479 ± 41 | 1.37 ± 0.10 | 39.18 ± 1.54 | 12.2 | 0.41 |
| HRP 67% | Putrescine | 287 ± 12 | 3.84 ± 0.06 | 183.28 ± 0.61 | 57.0 | 0.08 |
| | $H_2O_2$ | 211 ± 18 | 4.95 ± 0.15 | 321.36 ± 1.24 | — | — |

Redox hydrogel based biosensors were optimised in order to determine the influence of the redox polycation and the crosslinking agent. Table II shows the obtained results.

If the diffusion barrier increased with the number of added components on the electrode surface, a tendency reflected in the change of the apparent Michaelis-Menten constants. $K_m^{app}$ constant was increased with about 171% for histamine and 125% for putrescine. The introduction of the electrochemical mediator caused a considerable improvement in the bioelectrocatalytic efficiency, as can be seen from increase in the $I_{max}$ with 262% for histamine and 141% for putrescine and the sensitivity values with 33% for histamine and 7% for putrescine.

The hydrogen peroxide sensitivity remains practically unchanged. The detection limit and also the dynamic range for the studied analytes have also been improved in the case of type II electrodes.

In the table DR is the dynamic range and all the other symbols are the same as in Table I.

TABLE II

| Type of electrode | Analyte | $K_m^{app}$ ($\mu M$) | $I_{max}$ ($\mu A$) | S (mA/Mcm$^2$) | C % | DL ($\mu M$) | DR ($\mu M$) |
|---|---|---|---|---|---|---|---|
| Type I | Histamine | 332 ± 17 | 1.34 ± 0.02 | 55.29 ± 0.73 | 16.74 | 0.16 | 1–100 |
| | Putrescine | 227 ± 16 | 3.01 ± 0.07 | 181.64 ± 1.01 | 55.01 | 0.06 | 1–100 |
| | $H_2O_2$ | 112 ± 8 | 2.70 ± 0.06 | 330.14 ± 1.02 | | | 1–100 |
| Type II | Histamine | 901 ± 85 | 4.85 ± 0.41 | 3.874 ± 1.73 | 23.07 | 0.33 | 1–150 |
| | Putrescine | 512 ± 40 | 7.26 ± 0.53 | 194.11 ± 1.37 | 60.73 | 0.17 | 1–400 |
| | $H_2O_2$ | 977 ± 92 | 22.8 ± 1.68 | 319.59 ± 1.63 | | | 1–250 |

The effect of the coating procedure for the type II and type III biosensors was also studied. Besides coating with a premixed solutions of all four components, different possibilities of sequential coatings of the electrode surface, were also studied, see Table III. Both HRP and AO can be electrically wired to the redox polymer, and thus cause a partial short-circuit, when all components are mixed together. This was confirmed for the main substrate, putrescine, for which an increase in sensitivity of about 30% was observed for the two layer electrodes (type III), compared to the one-layer electrodes (type II).

No considerable change was observed for the other substrate histamine, the slight decrease in sensitivity being not representative considering, the differences of about 10–15% in electrode preparation. Clearly, the less sensitive electrode configuration is represented by type III d type electrodes, for which the bias currents due to the wiring of AO are the most explicit. Considering the simplicity of electrode preparation and the small differences in the electrode characteristics between type II and type III electrodes, type II was chosen as optimal electrode design.

TABLE III

| Type of electrode | Analyte | $K_m^{app}$ ($\mu M$) | $I_{max}$ ($\mu A$) | S (mA/Mcm$^2$) |
|---|---|---|---|---|
| Type II | Histamine | 901 ± 85 | 4.85 ± 0.41 | 67.65 ± 1.73 |
| | Putrescine | 512 ± 40 | 7.26 ± 0.53 | 194.24 ± 1.46 |
| Type IIIa | Histamine | 789 ± 35 | 3.56 ± 0.08 | 61.80 ± 0.68 |
| | Putrescine | 449 ± 34 | 7.72 ± 0.69 | 235.53 ± 1.60 |
| Type IIIb | Histamine | 687 ± 47 | 2.66 ± 0.24 | 53.03 ± 1.55 |
| | Putrescine | 473 ± 28 | 2.04 ± 0.13 | 59.08 ± 1.19 |

TABLE III-continued

| Type of electrode | Analyte | $K_m^{app}$ ($\mu M$) | $I_{max}$ ($\mu A$) | S (mA/Mcm$^2$) |
|---|---|---|---|---|
| Type IIIc | Histamine | 689 ± 33 | 2.17 ± 0.06 | 43.14 ± 0.75 |
| | Putrescine | 422 ± 35 | 7.83 ± 0.82 | 254.17 ± 1.82 |
| Type IIId | Histamine | 649 ± 19 | 1.90 ± 0.02 | 40.10 ± 0.42 |
| | Putrescine | 425 ± 24 | 2.14 ± 0.20 | 68.97 ± 1.49 |

The influence of various components of the redox hydrogel on the biosensor characteristics is shown in Table IV. The increasing $K_m^{app}$ in the presence of both $PVI_{13}$-dmeOs and PEGDGE demonstrated that the diffusion of the substrate was limited. This was because of the barrier formed by the mediator and/or cross-linking agent (rigidity of the redox hydrogel) on the surface of the electrode, which also resulted in an increased linear dynamic range. On the other hand, in the presence of crosslinked redox polycationic mediator (PVI$_3$-dmeOs), the I$_{max}$ value was 100% increased suggesting that the final reduction step of the topa cofactor on the electrode surface is the rate-limiting step in the absence of the mediator.

Table IV summarizes the response characteristics of different AO biosensors. The AO, PVI$_{13}$-dmeOs and PEGDGE concentrations were 5 mg/ml, 2 mg/ml and 0.5 mg/ml, respectively.

TABLE IV

| Type of electrode | $K_m^{app}$ ($\mu$M) | $I_{max}$ (nA) | S (mA/Mcm$^2$) | DL ($\mu$M) | DR ($\mu$M) |
|---|---|---|---|---|---|
| AO | 375 ± 34 | 164 ± 6.5 | 5.99 ± 0.09 | 2.7 | 10–100 |
| AO + PEGDGE | 755 ± 38 | 185 ± 5.0 | 3.35 ± 0.05 | 4.5 | 10–150 |
| AO + PVI$_{13}$-dmeOs | 770 ± 14 | 235 ± 2.4 | 4.18 ± 0.02 | 3.7 | 10–150 |
| AO + PVI$_{13}$-dmeOS + PEGDGE | 730 ± 33 | 360 ± 8.0 | 6.76 ± 0.05 | 2.2 | 10–200 |

The bi-enzyme electrodes were optimised with regard to several parameters, e.g. working potential, flow rate, influence of various enzyme ratios and electrode coating procedure.

Figure 1:
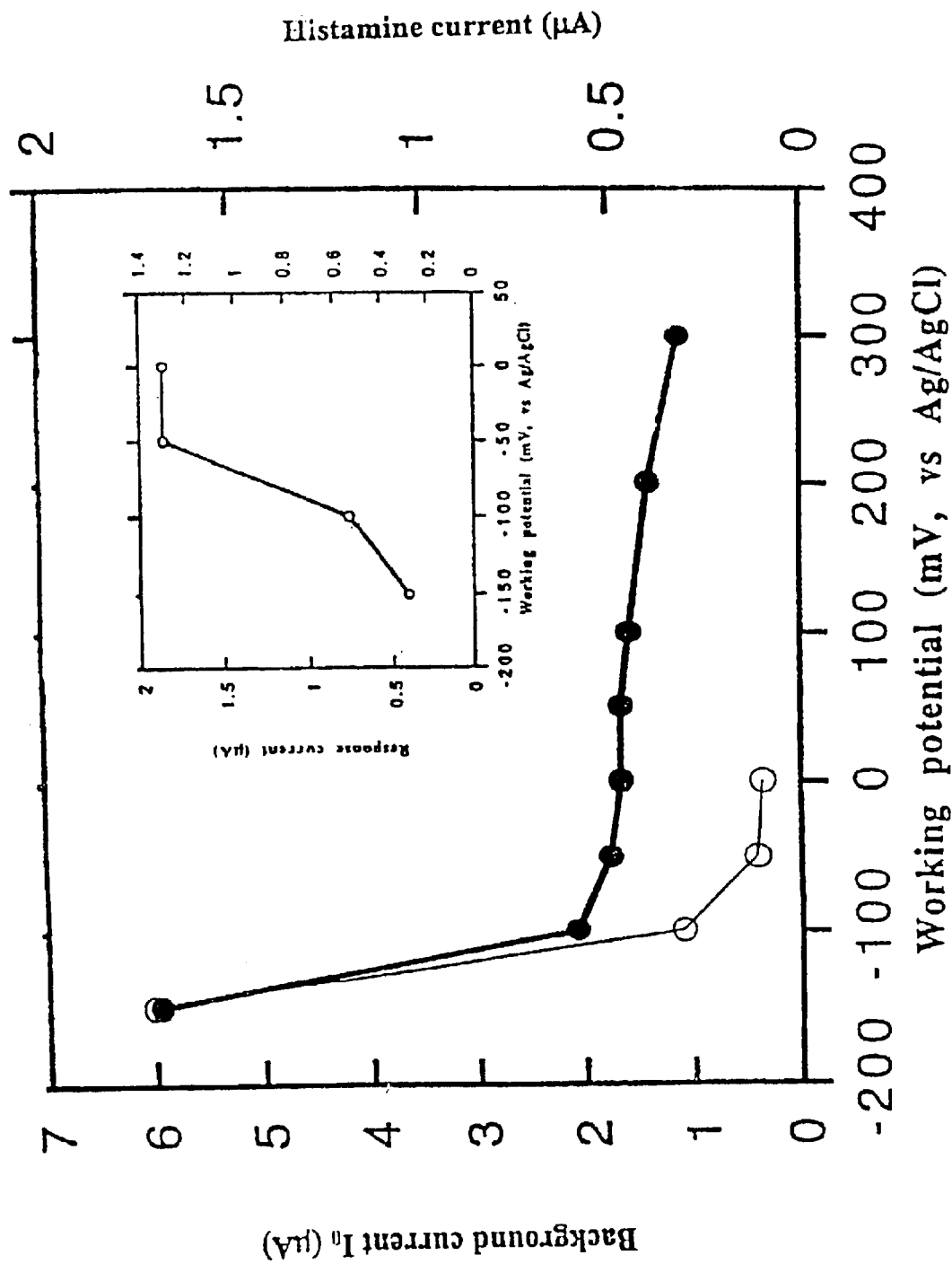
FIG. 1: Shows a voltammogram for 100 $\mu$M histamine using an AO-HRP modified graphite electrode (I)

Hydrodynamic voltammograms were recorded using 100 $\mu$M histamine as substrate and using an AO-HRP-modified type I electrodes in order to establish the optimal working potential. The voltammogram, together with the ratio between the response and the background current obtained in the same conditions, respectively, are shown in FIG. 1. Although the response of the biosensor drastically increased when the applied potential was below –100 mV so did the background current, which demonstrates a possible oxygen reduction interference with the biosensing process. A potential of –50 mV vs. Ag/AgCl was chosen as a compromise between the response and the background current. The background current obtained in the same condition (I$_0$), and the ratio between them (I/I$_0$). Conditions: electrode Type I, AO: HRP 1:1 (w/w), flow rate 0,5 ml/min.

Figure 2:
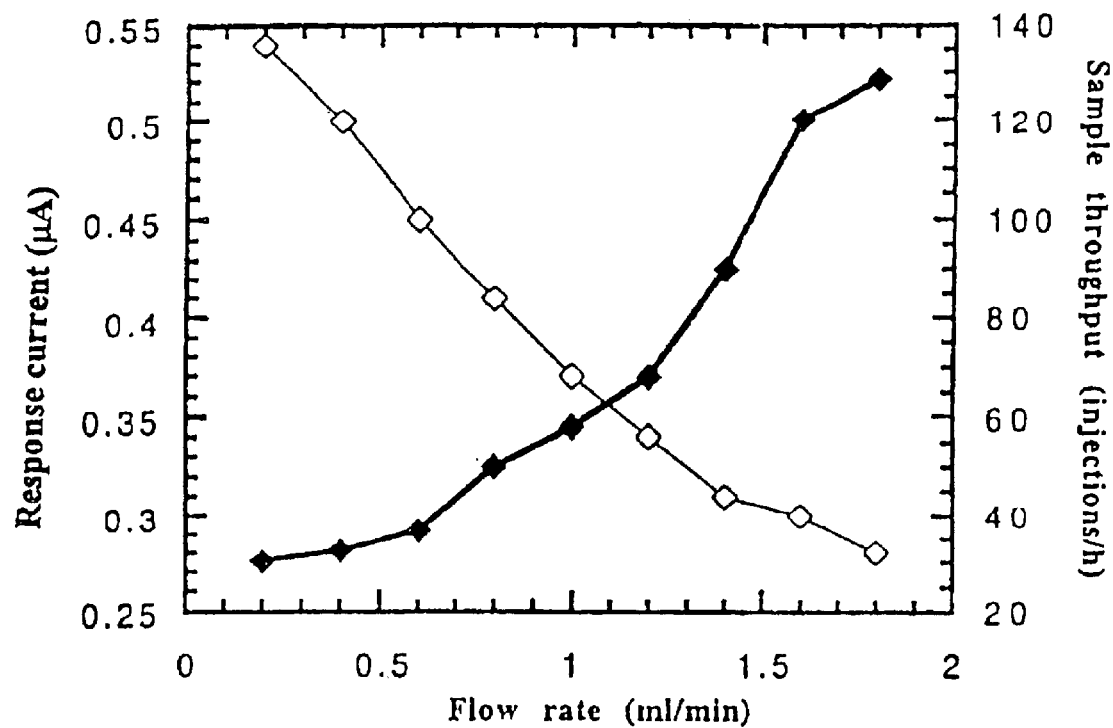
FIG. 2: Shows the effect of the flow rate on the response current and sample throughput of Type I biosensors.

The influence of carrier flow rate on the biosensor response for histamine was also considered for type I electrodes, the results are presented in FIG. 2. The decrease in peak height with the increase in flow rate demonstrates a limitation due either to the bioconversion of the amine substrate by AO or to the reduction of H$_2$O$_2$ by the direct electron transfer between HRP and the graphite electrode. According to the obtained results an optimal working flow rate was chosen to be 0.5 ml/min, as a compromise between the biosensor kinetics and its sample throughput. Conditions: injections of 100 $\mu$M histamine, AO: HRP 1:1 (w/w), applied potential –50 mV vs. Ag/AgCl.

Figure 3:
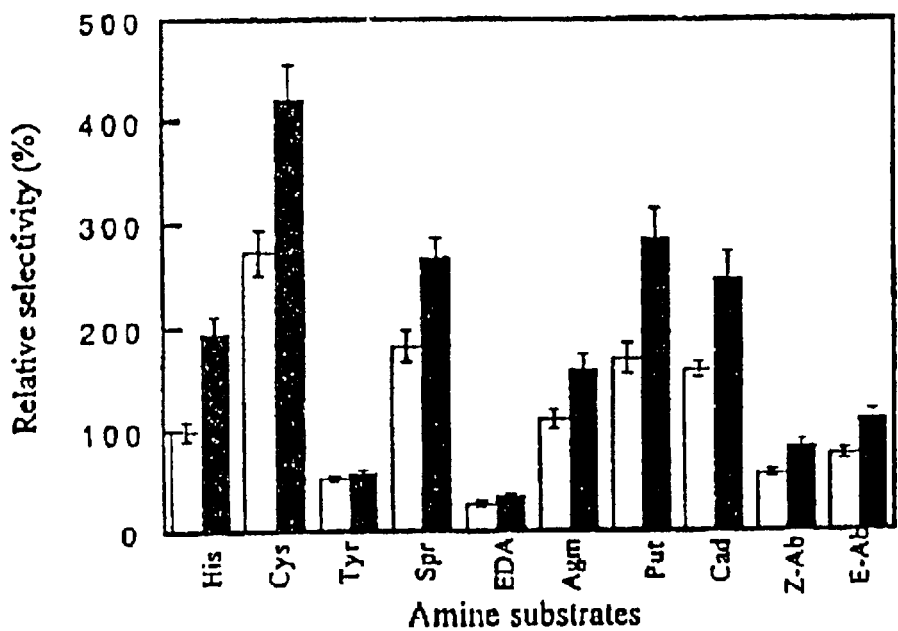
FIG. 3: Shows the relative selectivity for different amine oxidase substrates, using histamine as reference compound, recorded for Type I (white) and Type II (black) electrodes.

Type II biosensors were further characterized with regard to selectivity, response time, operational and storage stability. FIG. 3 shows the relative selectivity for different AO substrates, using histamine as a reference compound, since it is a biomarker of major interest. As seen, the response for aliphatic amines is generally higher than those observed for the aromatic ones. Also, type II biosensors yielded higher sensitivities than type I ones, probably caused by better electron-transfer kinetics.

The response time of the sensor, calculated as the time elapsed between 5% and 95% of response height, was fast (less than 1 min).

The operational stability of the biosensor was studied both for histamine and putrescine as substrate. The response current of the bi-enzymatic enzyme electrode decreased with about 30% and 50% for histamine and putrescine, respectively. This after 10 h of continues operation with a sample throughput of 30 injections/h. The storage stability of the electrodes was good, a decrease of only about 10% and 15% being observed fore histamane and putrescine, respectively, after 10 days of storage.

The substrates are histamine His, cystamine Cys, tyramine Tyr, spermidine Spr, ethylenediamine EDA, agmatine Agm, putrescine Put, cadaverine Cad, Z-Ab-Z-1,4-diamino-2-butene and E-Ab-E1,4-diamino-2-butane.

Figure 4:
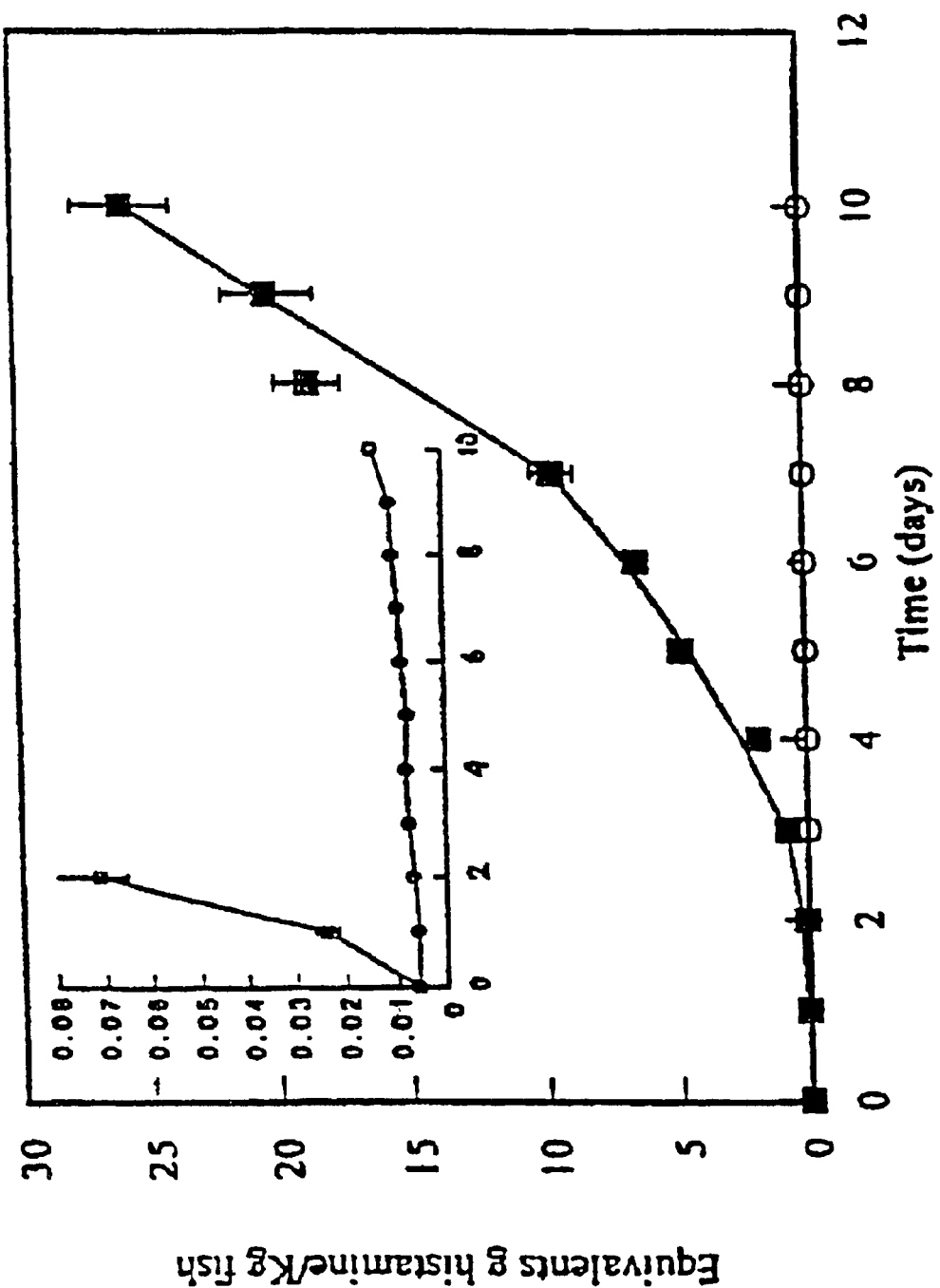
FIG. 4: Shows the monitoring of freshness in fish samples using Type II electrodes. The total amine concentration is expressed in histamine equivalent units.

The optimised biosensor was considered for monitoring biogenetic amines in real samples. The differentiation between the signals given by different amines is not possible, only the total amine content in a sample could be determined. Triplets of 1.0 g of fish samples were taken from fish-muscles from tro-bot—Psetta maxima—and were kept in different conditions. The samples were homogenised in 10 ml PB. The homogenates were centrifuged at 13000 g for 60 min at 4° C. The supernatants were separated and immediately analysed by direct injection into the flow system. The fish-muscle samples, which had been kept both at, 4° C. and 25° C. for 10 days, were analysed after extraction in PB by direct injection in the flow system. The total amine content expressed in histamine equivalents is presented in FIG. 4. The maximum accepted limit for total amine concentration in food products is 100 to 200 mg/kg samples, and a concentration of 1000 mg/kg is considered to be toxic. After 3 days of storage at room temperature, the fish-samples become improper to consume, while even after 10 days of storage at 4° C. there are not any major changes in the total amine concentration.

What is claimed is:

1. A method for the detection or determination of histamine in a sample of microdialysates or dialysates, comprising the steps of:

(A) applying said sample to a biosensor comprising an electrode and (i) a mono-enzyme system of an amine oxidase, which is a copper-containing grass pea oxidase (E. C. 1.4.3.6) or (ii) a bi-enzyme system of an amine oxidase, which is a copper-containing grass pea oxidase (E.C. 1.4.3.6), coupled with horseradish, soybean, tobacco, sweet potato or palmtree peroxidase; wherein said electrode is a carbon/graphite based electrode, and whereby said amine oxidase is cross-linked to the electrode into an osmium based redox polymer; and (B) detecting an electrical output from said biosensor.

2. The method according to claim 1, wherein the peroxidase is horseradish peroxidase.

3. The method according to claim 1, wherein the osmium based redox polymer comprises poly(1-vinylimidazole) complexed with [Os(4,4'-dimethyl-bi-pyridin)$_2$Cl]$^{+/2+}$ and polyethyleneglycol)diglycidyl ether as the cross-linking agent.

4. The method according to claim 1, wherein biosensor is of Type I, Type II or Type III type of biosensor, wherein:

Type I is the mono-enzyme or the bi-enzyme system is added directly into the electrode surface; or Type II is the mono-enzyme or the bi-enzyme system is entrapped in the osmium based redox polymer added on the surface of the electrode; or Type III is the mono-enzyme or the bi-enzyme system and the osmium based redox polymer forms sequential coatings added on the surface of the electrode.

5. The method according to claim 4, wherein the biosensor of Type III is one of Type III a, Type III b, Type III c or Type III d, wherein:

Type III a is a second coating of the mono-enzyme is coating a dried layer of peroxidase and redox hydrogel; or Type III b is a second coating of peroxidase and redox hydrogel is coating a dried layer of the mono-enzyme; or Type III c is a second coating of the mono-enzyme entrapped in redox hydrogel is coating a dried layer of peroxidase; or Type III d is a second coating of peroxidase is coating a dried layer of mono-enzyme entrapped in redox hydrogel.

6. The method according to claim 2, wherein the weight ratio of amine oxidase to horseradish peroxidase is 80:20.

* * * * *